United States Patent

Arai et al.

[11] Patent Number: 5,218,126
[45] Date of Patent: Jun. 8, 1993

[54] HALOGEN SUBSTITUTED MITOMYCIN DERIVATIVES

[75] Inventors: Hitoshi Arai, Shizuoka; Masaji Kasai, Fujisawa; Katsushige Gomi, Susono; Tadashi Ashizawa, Numazu, all of Japan

[73] Assignee: Kyowa Hakko Kogyo Co., Ltd., Tokyo, Japan

[21] Appl. No.: 755,528

[22] Filed: Sep. 5, 1991

[30] Foreign Application Priority Data

Sep. 5, 1990 [JP] Japan ................................ 2-235294

[51] Int. Cl.$^5$ ............................................ C07D 487/04
[52] U.S. Cl. .................................................. 548/422
[58] Field of Search ......................................... 548/422

[56] References Cited

U.S. PATENT DOCUMENTS 4,880,825  11/1989  Kasai et al. .................. 548/422

FOREIGN PATENT DOCUMENTS 0359480  8/1989  European Pat. Off. .
5059365  5/1975  Japan .

OTHER PUBLICATIONS

Iyengar et al., J. Med. Chem (1983) No. 26, pp. 1453–1457.
Kinoshita et al., J. Med. Chem (1971), vol. 14, No. 2, pp. 103–109.

Primary Examiner—Joseph Paul Brust
Assistant Examiner—Mary Susan H. Gabilan
Attorney, Agent, or Firm—Antonelli, Terry, Stout & Kraus

[57] ABSTRACT

Disclosed are mitomycin derivatives of formula (I):

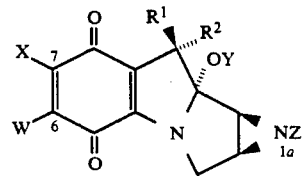

where W represents halogen; X represents methoxy, amino or ethylenimino; Y represents hydrogen or methyl; Z represents hydrogen or methyl; and one of $R^1$ and $R^2$ represents carbamoyloxymethyl, and the other represents hydrogen. The derivatives are usable as an antitumor and antibacterial agent.

6 Claims, No Drawings

HALOGEN SUBSTITUTED MITOMYCIN DERIVATIVES

FIELD OF THE INVENTION

The present invention relates to novel mitomycin derivatives having antitumor and antibacterial activities.

BACKGROUND OF THE INVENTION

Mitomycins are known as antibiotics having, in general, antibacterial and antitumor activities. Among known mitomycin derivatives, are those where one hydrogen in the methyl group at the 6-position is substituted by alkoxy or alkylthio, which derivatives are illustrated in JP-A-167282/90, and represented by the following formula:

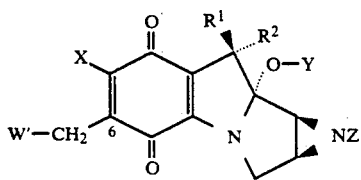

in which W' represents alkoxy or alkylthio.

The term "JP-A" as referred to herein means "Japanese Published Unexamined Patent Application".

SUMMARY OF THE INVENTION

The object of the present invention is to provide novel mitomycin derivatives in which the 6-position is substituted by hydrogen or halogen.

Specifically, the present invention provides a novel mitomycin derivative represented by the formula (I):

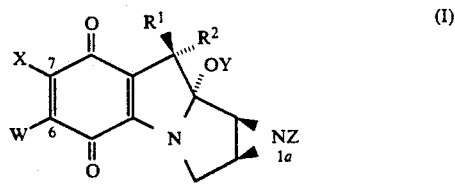

where W represents hydrogen or halogen; X represents methoxy, amino or ethylenimino; Y represents hydrogen or methyl; Z represents hydrogen or methyl; and one of $R^1$ and $R^2$ represents carbamoyloxymethyl and the other represents hydrogen.

DETAILED DESCRIPTION OF THE INVENTION

The Compound represented by formula (I) is referred to as Compound (I); and hereunder the same shall apply to other compounds of other formulae.

The halogen as referred to for defining the substituents of formula (I) includes chlorine, bromine and iodine atoms.

Methods of preparing Compounds (I) are mentioned below.

Preparation Method 1

Compound (Ia), which is Compound (I) where X is amino and Compound (Ib), which is Compound (I) where X is methoxy, are produced by the following reaction steps:

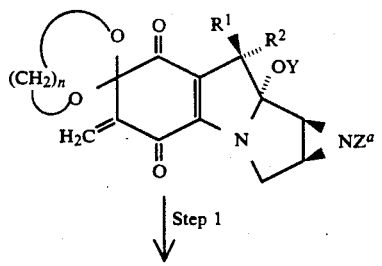

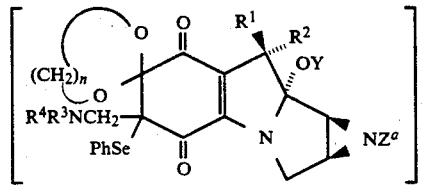

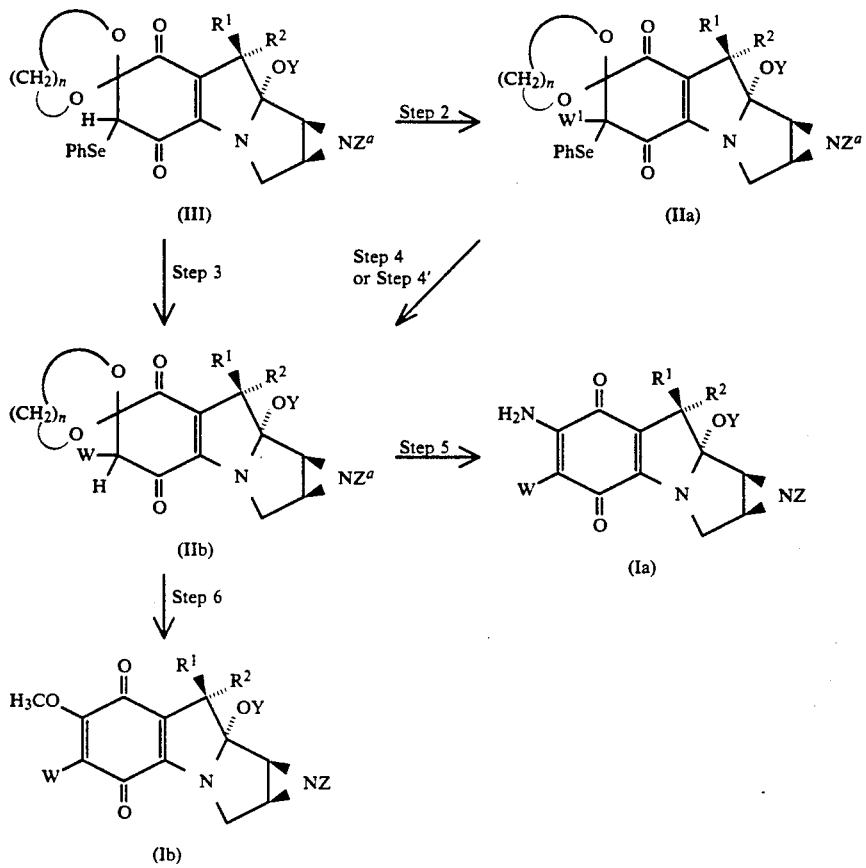

(III)

(IIa)

(IIb)

(Ia)

(Ib)

In the above formulae, $R^3$ and $R^4$ may be the same or different and each represents lower alkyl or benzyl; $W^1$ represents chlorine, bromine or iodine; $Z^a$ represents hydrogen, methyl or acetyl; n represents an integer of 2 or 3; Ph represents phenyl; and $R^1$, $R^2$, W, X, Y and Z have the same meanings as mentioned above.

Step 1

Compound (III) can be prepared by reacting Compound (IV) [JP-A-70490/89] with a selenoating agent represented by formula (VI):

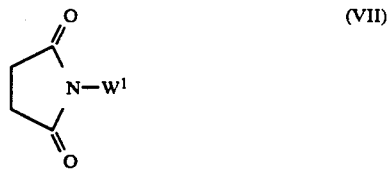

(VI)

[where $R^3$ and $R^4$ have the same meanings as mentioned above] in an inert solvent, via Compound (V) as an intermediate. As the solvent used in the reaction, mention may be made of ether, tetrahydrofuran, methylene chloride, chloroform and n-hexane singly or in combination. Compound (VI) is used generally in an amount of from 0.1 to 3.0 equivalents, preferably 0.6 to 1.2 equivalents, based on Compound (IV). The reaction is carried out at a temperature of −40° C. to 60° C., preferably at 0° C. to 25° C., for a period of from 30 minutes to 10 hours.

Step 2

Compounds (IIa) can be prepared by reacting Compound (III) with a halogenating agent represented by formula (VII):

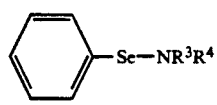

(VII)

[where $W^1$ has the same meaning as mentioned above] in an inert solvent in the presence or absence of a base.

As the reaction solvent, mention may be made of ether, tetrahydrofuran, acetone, methylene chloride, chloroform and dimethylformamide. Such solvents can be used singly or in combination of two or more of them. As the base used in the reaction, mention may be made of inorganic bases such as sodium bicarbonate and potassium carbonate, etc.; organic bases such as pyridine and triethylamine. The base may be used in the reaction in an excessive amount, preferably in an amount of 2 to 3 equivalents based on Compound (III). Compound (VII) is used generally in an excessive amount, preferably in an amount of 1.5 to 3.0 equivalents based on Compound (III).

The reaction is generally conducted at a temperature of 0° C. to 30° C. for a period of one hour to 24 hours.

Step 3

Compounds (IIb) [where W is hydrogen] can be prepared by reducing Compound (III) with a reducing agent in an inert solvent with or without a radical initiator.

As the reducing agent used in the reaction, tributyl tin hydride or triphenyl tin hydride is used. The agent is used in an amount of one or more equivalents based on Compound (III), preferably 2 to 10 equivalents. As the radical initiator, triethyl borane or azobisisobutyronitrile, etc. may be used. It is used in an amount of one or less equivalent based on Compound (III), preferably from 0.1 to 1.0 equivalent.

As the solvent for the reaction, benzene, toluene, ether, tetrahydrofuran, etc. may be used.

The reaction is carried out at a temperature of $-40°$ C. to 120° C. and completed in one to 24 hours.

Step 4

Compounds (IIb) where W is halogen can be prepared by reducing Compound (IIa) with a reducing agent in an inert solvent.

As the reducing agent, tributyl tin hydride, triphenyl tin hydride, etc. may be used in an amount of one or more equivalents based on Compound (IIa), preferably 1.0 to 3.0 equivalents.

The same solvents as used in Step 3 of Preparation Method 1 can be used. The reaction is carried out at a temperature of 0° C. to 120° C., preferably from 30° C. to 60° C., and completed in 30 minutes to 10 hours.

Step 4'

Compound (IIb) [where W is halogen] can be also prepared by reacting Compound (IIa) with dimedone in the presence of a base in an inert solvent.

The amount of dimedone used in the reaction is one or more equivalents based on Compound (IIa).

As the inert solvent, mention may be made of methanol, tetrahydrofuran, etc.

As the base, mention may be made of an inorganic base such as potassium carbonate, etc.; an organic base such as triethylamine, etc. The base is used in an excessive amount to dimedone.

The reaction is carried at 0° C. to 50° C., preferably 10° C. to 30° C., and completed in 5 minutes to 3 hours.

Step 5

Compound (Ia) is prepared by reacting Compound (IIb) with ammonia in an inert solvent.

Any solvent can be used so long as Compound (IIb) is dissolved in the solvent. As the solvent, alcohols such as methanol and ethanol, ethers such as ether and tetrahydrofuran, halogenated alkanes such as methylene chloride and chloroform, as well as acetonitrile, dimethylformamide and dimethylsulfoxide, may be used singly or in combination. The reaction is carried out at a temperature of 0° C. to 30° C. and completed in one hour to 20 hours.

Step 6

Compound (Ib) is prepared by reacting Compound (IIb) with a base in methanol.

As the base in the reaction, mention may be made of a compound represented by formula $R^c$-O-M (where $R^c$ represents lower alkyl having from 1 to 4 carbon atoms; and M represents an alkali metal or an alkaline earth metal); alkali metal or alkaline earth metal hydroxides such as potassium hydroxide and sodium hydroxide; carbonates and bicarbonates such as potassium carbonate and sodium bicarbonate; tertiary amines such as triethylamine; and quaternary ammonium hydroxides such as tetrabutylammonium hydroxide, etc.

The base is used in the reaction in an amount of 0.001 to 10 equivalents, preferably 0.10 to 3 equivalents based on Compound (IIb).

The reaction is carried out at a temperature of 0° C. to 30° C. and completed in one hour to 24 hours. In Steps 5 and 6, Compound (IIb) where Z is acetyl, is deacetylated under the above-mentioned reaction condition to give the corresponding Compounds (Ia) and (Ib), where Z is hydrogen.

Preparation Method 2

Compound (Iaa), which is Compound (I) where X is an amino and W is chlorine, bromine or iodine, can be prepared by the following reaction steps.

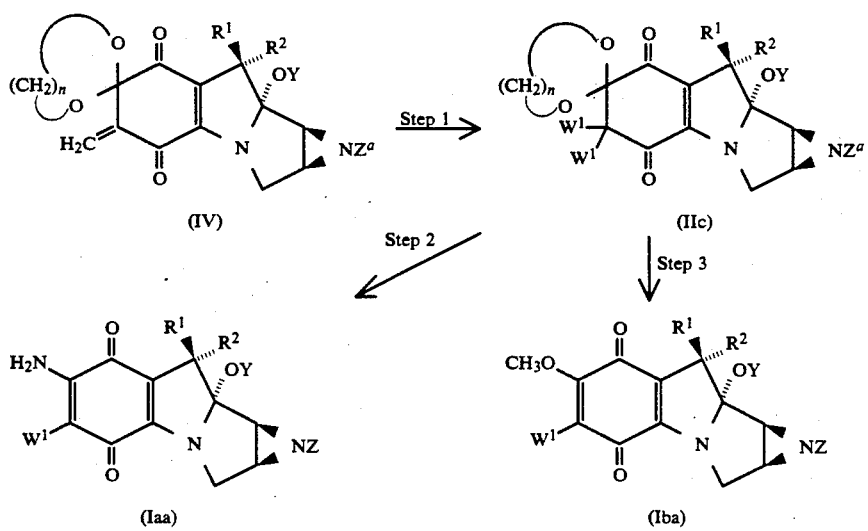

In the formulae, $W^1$ represents chlorine, bromine or iodine, and Y, Z, $Z^a$, $R^1$, $R^2$ and n have the same meanings as those mentioned above.

Step 1

Compound (IIc) is prepared by reacting Compound (IV) with the halogenating agent (VII) in the presence of a base in an inert solvent.

As the solvent, ether, tetrahydrofuran, methylene chloride, chloroform and dimethylformamide, etc. may be used singly or in combination. As the base, for example, mention may be made of secondary amines such as dimethylamine, diethylamine, benzylmethylamine, diisopropylamine, pyrrolidine, piperidine and morpholine, etc.

Compound (VII) is generally used in an excessive amount preferably in an amount of 2 to 3 equivalents based on Compound (IV). The base is used in an excessive amount, preferably in an amount of 1 to 5 equivalents based on Compound (IV).

The reaction is carried out at a temperature of 0° C. to 30° C., and completed in 1 to 24 hours.

Step 2

Compound (Iaa) is prepared by reacting Compound (IIc) with ammonia in an inert solvent in the presence of dimedone.

The same solvent as used in Step 4' of Preparation Method 1 can be used. Dimedone is used in an excessive amount preferably 2 to 5 equivalents based on Compound (IIc).

The reaction is carried out at a temperature of 0° C. to 30° C., and completed in 1 to 24 hours.

Step 3

Compound (Iba) is prepared by reacting Compound (IIc) with dimedone in the presence of a base in methanol.

The amount of dimedone used in the reaction is one or more equivalents based on Compound (IIc).

The base is used in the reaction in an excessive amount, preferably 1.5 to 3 equivalents based on dimedone.

The reaction is carried out at 0° C. to 50° C., preferably 10° C. to 30° C., and completed in 1 hour to 72 hours.

Compound (IIc), where $z^a$ is acetyl is simultaneously deacetylated under the above-mentioned reaction condition to give the corresponding products (Iaa) and (Iba) where Z is hydrogen.

Preparation Method 3

Compound (Id), which is Compound (I) where Z is methyl, is prepared by reacting Compound (Ic), which is Compound (I) where Z is hydrogen with methyl iodide in an inert solvent and in the presence of a base.

(Ic) → [CH₃I] → (Id)

In the formula, W, X, Y, $R^1$ and $R^2$ have the same meanings as mentioned above.

The same solvent and base as those used in Step 2 of Preparation Method 1 can be used.

The reaction is carried out at a temperature of 0° C. to 120° C., preferably 30° C. to 60° C., and completed in 1 to 30 hours.

Preparation Method 4

(Ib) → (Ie)

In the formula, W, Y, Z, $R^1$ and $R^2$ have the same meanings as those mentioned above.

Compound (Ie) is prepared by reacting Compound (Ib) with ethylenimine in an inert solvent. Ethylenimine is used in an excessive amount.

The same solvent as used in Step 5 of Preparation Method 1 can be used. The reaction is carried out at 0° C. to 50° C., preferably 10° C. to 30° C., and completed in 1 minute to 1 hour.

The intermediates and products to be produced in the above-mentioned preparation method can be isolated and purified by using various conventional purification methods which are generally employed in organic synthetic chemistry, for example, by neutralization, filtration, extraction, washing, drying, concentration, recrystallization and various chromatographies. In the case of intermediates they can be applied directly to the next step without further purification.

Compound (I) may be obtained in the form of adducts with water or various solvents, which are also within the scope of the present invention.

Specific examples of Compound (I) are mentioned in Table 1 below.

TABLE 1

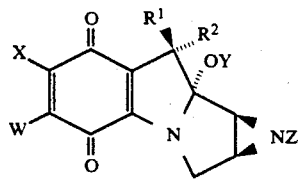

| Compound (Example) | W | X | Y | Z | R¹ | R² |
|---|---|---|---|---|---|---|
| 1 (1) | H | OCH₃ | CH₃ | H | CH₂OCONH₂ | H |
| 2 (2) | H | OCH₃ | H | CH₃ | H | CH₂OCONH₂ |
| 3 (3) | H | NH₂ | CH₃ | H | CH₂OCONH₂ | H |
| 4 (4) | H | NH₂ | H | CH₃ | H | CH₂OCONH₂ |
| 5 (5) | H | OCH₂ | CH₃ | CH₃ | CH₂OCONH₂ | H |
| 6 (6) | H | NH₂ | CH₃ | CH₃ | CH₂OCONH₂ | H |
| 7 (7) | Cl | NH₂ | CH₃ | H | CH₂OCONH₂ | H |
| 8 (8) | Br | NH₂ | CH₃ | H | CH₂OCONH₂ | H |
| 9 (9) | Br | NH₂ | H | CH₃ | H | CH₂OCONH₂ |
| 10 (10) | Cl | OCH₃ | CH₃ | H | CH₂OCONH₂ | H |
| 11 (11) | Br | OCH₃ | CH₃ | H | CH₂OCONH₂ | H |
| 12 (12) | Br | OCH₃ | H | CH₃ | H | CH₂OCONH₂ |
| 13 (13) | H | N◁ | CH₃ | H | CH₂OCONH₂ | H |

The anti-tumor activity and acute toxicity of typical examples of Compound (I) are described below.

Growth Inhibition Test on HeLa S₃ Cells

HeLa S₃ cells were suspended in an MEM medium containing 10% fetal calf serum and 2 mM glutamine at a concentration of $3 \times 10^4$ cells/ml, and 0.1 ml of the cell suspension was put into each well of a 96-well microtiter plate.

After culturing at 37° C. overnight in a carbon dioxide gas incubator, 0.05 ml of a test sample appropriately diluted with the medium was added to each well. The cells were further cultured for one hour in the carbon dioxide gas incubator and the culture supernatant was removed. The residue was washed once with a phosphate buffer saline [PBS(−)] and 0.1 ml of a fresh medium was added to each well, and the cells were further incubated at 37° C. for 72 hours in the carbon dioxide gas incubator. After removal of the supernatant, 0.1 ml of culture medium containing 0.02% Neutral Red was added to each well, and the cells were further incubated at 37° C. for one hour in the carbon dioxide gas incubator to stain the cells. After removal of the culture supernatant, each well was washed once with a physiological saline, and the dye was extracted with 0.001N HCl/30% methanol. Absorbance of the extract at 550 nm was measured with a microplate reader. The cell growth inhibition percentage was calculated according to the following formula from the absorbance of the extract of the cells treated with the test compound in various concentrations and that of intact cells.

Cell Growth Inhibition Percentage (%) =

$$100 - \frac{\text{(absorbance of cells treated with test compound)} - \text{(absorbance of cell-free well)}}{\text{(absorbance of intact cells)} - \text{(absorbance of cell-free well)}} \times 100$$

From the cell growth inhibition percentage thus obtained, the concentration of the test compound which inhibits cell growth by 50% (IC₅₀) was determined.

The results are shown in Table 2.

TABLE 2

| Test Compound | IC₅₀ (μM) |
|---|---|
| 1 | 0.21 |
| 2 | >10 |
| 3 | 2.2 |
| 4 | >31 |
| 5 | 0.13 |
| 6 | 7.3 |
| 7 | 0.55 |
| 8 | 0.72 |

TEST EXAMPLE 2

Anti-tumor Activity to Sarcoma 180 Solid Tumor $5 \times 10^6$ Sarcoma 180 cells were abdominally implanted into a ddY mouse and the cells were collected from the ascites of the mouse 7 days after the implantation. The cells were washed once with a sterilized physiological saline solution and then suspended in a sterilized physiological saline solution to prepare a cell suspension of $5 \times 10^7$ cells/ml. 0.1 ml of the cell suspension was subcutaneously implanted into the right axiallary space of male ddY mice weighting 20±2 g.

A test compound was dissolved in a physiological saline solution or a Tween 80-containing physiological saline solution, and 0.1 to 0.2 ml of the solution was intravenously injected to five mice as one group 24 hours after the implatation of the tumor cells.

The anti-tumor activity of the test compound was determined by measuring the major diameter (a) and the minor diameter (b) of the tumor 7 days after the implantation of tumor cells, and the value of $(a \times b^2/2)$, which corresponds to the volume of the tumor, was calculated. The intended anti-tumor activity is represented by a ratio of T/C, in which C indicates the tumor volume of mice of the control group to which no test compound was administered and T indicates the tumor volume of mice of the test group to which the test compound was administered. T/C at each dose given was plotted in a graph in which T/C is shown by an ordinary scale on the vertical axis and a dose is shown by a logarithmic scale on the horizontal axis. The relation between the dose and T/C was determined to be a straight line by the least-squares method. From the regression formula of the straight line thus obtained, the dose of showing T/C=0.5 is calculated to give $ED_{50}$.

The results are shown in Table 3.

TABLE 3

| Test Compound | $ED_{50}$ (mg/Kg) |
|---|---|
| 1 | 1.6 |
| 2 | 11 |
| 3 | 2.6 |
| 4 | 33 |
| 5 | 7.1 |
| 6 | 8.4 |
| 8 | 1.6 |

TEST EXAMPLE 3

Acute Toxicity

A test compound was intravenously injected once to five ddY mice as one group. After the administration, the mice were observed for 14 days and deaths were noted. $LD_{50}$ was calculated from the death rate of each group according to the Behrens Kaerber's method.

The results are shown in Table 4.

TABLE 4

| Test Compound | $LD_{50}$ (mg/Kg) |
|---|---|
| 1 | 2.8 |
| 2 | >20 |
| 3 | 9.7 |
| 4 | >100 |
| 5 | 26 |
| 6 | 18 |
| 8 | 3.2 |

The compounds obtained by the present invention are useful as anti-tumor agents, which can be used directly as they are, or in various forms for administration. For instance, where Compounds (I) are used in the form of an injection, they are dissolved in a diluent which is conventionally used in the art, such as a physiological saline solution, or glucose, lactose or mannitol solution for injection. Alternatively, the compounds may be freeze-dried according to the Japanese Pharmacopoeia to give a powder for injection or may be prepared into injectable powder by adding sodium chloride thereto. In addition, the injection may also contain an auxiliary agent such as polyethylene glycol or HCO-60 (surfactant manufactured by Nikko Chemical Co.), as well as carrier such as ethanol and/or liposome or cyclodextrin. The injections are generally used for intravenous administration, but may also be used for intra-arterial administration, intraperitoneal administration or intra-thoracical administration.

Where the compounds of formula (I) are used as a peroral drug, they may also be formed into tablets, granules, powder or syrup for oral administration with an appropriate excipient, disintegrator, binder or lubricant in a conventional manner. Further, Compounds (I) may be mixed with a conventionally used carrier and formed into suppositories for rectal administration in a conventional manner.

Dosage may appropriately vary according to the administration schedule, the kind of Compounds (I), and the age and condition of a patient. Administration schedule may also be varied according to the condition of a patient and the dosage. For example, the compounds can be intermittently administered in a dose of 0.06 to 6 mg/kg once a week or once every three weeks.

Certain embodiments of the invention are illustrated in the following examples.

Physicochemical data of each compound were obtained by using the following devices.

$^1$H-NMR: JEOL, Ltd. JNM-GX270(270 MHz)
VARIAN EM390(90 MHz)
Bruker AM400(400 MHz)

MS: JEOL, Ltd. JSM-D300(measured by the FAB or EI method)

IR: Nihon Bunko K.K., Japan IR-810(measured by the KBr method)

TLC: silica gel Art5715(manufactured by Merck Inc.)

Preparative TLC: silica gel Art13794(manufactured by Merck Inc.)

EXAMPLE 1

Synthesis of 6-demethylmitomycin A (Compound 1)

47.5 mg of Compound "e" obtained in Reference Example 5 was dissolved in 10 ml of methanol, and 5 mg of potassium carbonate was added to the solution. The reaction mixture was stirred for 2 hours and 20 minutes at 25° C.

The reaction mixture was diluted with a phosphate buffer (0.1M; pH7) and extracted with chloroform several times. The extract obtained was washed with a saturated saline solution, and dried over anhydrous sodium sulfate. After the desiccant was removed by filtration, the solvent was distilled off. The residue obtained was purified by column chromatography (silica gel; chloroform: methanol=20:1) to obtain a scarlet fraction, and the solvent was distilled off under reduced pressure. The residue obtained was dissolved in a small amount of dichloromethane, and n-hexane was added to the solution to give a powder. After the solvent was distilled off, the residue was dried thoroughly in vacuo to give 18.9 mg (yield 48%) of Compound 1 as a scarlet powder.

TLC: Rf=0.27 (chloroform:methanol=9:1)

FAB-MS(m/z): 336(M+ +1); $C_{15}H_{17}N_3O_6$: 335

IR (cm$^{-1}$): 3450, 3350, 3290, 3200, 2940, 1720, 1650, 1570, 1450, 1340, 1310, 1240, 1070, 1050

$^1$H-NMR: δ, ppm(270 MHz, pyridine-d$_5$) 2.17(bs, 1H), 2.77(bs, 1H), 3.17(bs, 1H), 3.23(s, 3H), 3.55(bd, J=Ca. 13 Hz, 1H), 3.58(s, 3H), 4.03(dd, J=4.2 and 11.2 Hz, 1H), 4.29(d, J=12.6 Hz, 1H), 5.10(dd, J=11 Hz, 1H), 5.42(dd, J=4.4 and 10.4 Hz, 1H), 5.69(s, 1H), 7.4~7.9(bs, 2H)

EXAMPLE 2

Synthesis of 6-demethylmitomycin B (Compound 2)

49.4 mg of Compound "f" obtained in Reference Example 6 was dissolved in 25 ml of methanol, and 10 mg of potassium carbonate was added to the solution. The reaction mixture was stirred for 1 hour and 30 minutes at 25° C.

The resultant reaction mixture was diluted with a phosphate buffer (0.1M; pH7) and extracted with chloroform several times. The solution obtained was dried over anhydrous sodium sulfate. After the desiccant was removed by filtration, the solvent was distilled off.

The residue obtained was purified by column chromatography (silica gel; chloroform:methanol=10:2) to obtain reddish violet fractions. The solvent of these fractions was distilled off under reduced pressure. The residue obtained was dissolved in a small amount of dichloromethane, and allowed to stand to give 26.1 mg (yield 58%) of Compound 2 as reddish violet prisms.

n-Hexane was added to the filtrate above to give another crop as a powder. After the solvent was distilled off, the residue was dried to give 3.7 mg (yield 8.2%) of Compound 2 as reddish violet prisms.

TLC: Rf=0.29(chloroform:methanol=9:1)

FAB-MS (m/z): 336(M+ +1); $C_{15}H_{17}N_3O_6$: 335

IR (cm$^{-1}$): 3460, 3360, 3200, 2950, 1710, 1650, 1570, 1450, 1420, 1340, 1240, 1120, 1070, 1040, 1000

$^1$H-NMR: δ, ppm(270 MHz, pyridine-d$_5$) 2.14(s, 3H), 2.24(dd, J=1.7 and 4.7 Hz, 1H), 2.48(d, J=4.6 Hz, 1H), 3.50(s, 3H), 3.60(dd, J=1.8 and 12.6 Hz, 1H), 4.22(d, J=12.6 Hz, 1H), 4.25(dd, J=3.3 and 3.9 Hz, 1H), 5.24(bt, J=10 Hz, 1H), 5.45(dd, J=3.3 and 10.6 Hz, 1H), 5.61(s, 1H), 7.3~7.8(bs, 2H), 8.33(s, 1H)

EXAMPLE 3

Synthesis of 6-demethylmitomycin C (Compound 3)

32.8 mg of Compound "e" obtained in Reference Example 5 was dissolved in 5.0 ml of methanol, and 0.50 ml of an ammonia/methanol solution (6.1N) was added to the solution. The reaction mixture was allowed to stand for 3 hours and 15 minutes at 25° C.

Then, the solvent was distilled off, and the residue obtained was purified by column chromatography (silica gel; chloroform: methanol=from 9:1 to 4:1) to obtain violet fractions. The solvent of the fractions was distilled off, and the residue was dissolved in a methanol/chloroform solution. The resultant solution was allowed to stand to give 20.4 mg (yield 79%) of Compound 3 as violet prisms.

TLC: Rf=0.18 (chloroform:methanol=9:1)

FAB-MS(m/z): 321(M+ +1); $C_{14}H_{16}N_4O_5$: 320

IR (cm$^{-1}$): 3340, 3280, 2970, 2930, 1720, 1590, 1550, 1480, 1450, 1330, 1060

$^1$H-NMR: δ, ppm(270 MHz, DMSO-d$_6$) 1.80(bs, 1H), 2.71(bs, 1H), 2.81(bs, 1H), 3.12(s, 3H), 3.3~3.4(m, 2H), 4.01(d, J=13.0 Hz, 1H), 4.09(m, 1H), 4.54(dd, J=4.3 and 10.3 Hz, 1H), 5.23(s, 1H), 6.3~6.8(bs, 2H), 6.9~7.4(bs, 1H), 7.7~8.4(bs, 1H)

EXAMPLE 4

Synthesis of 6-demethylmitomycin D (Compound 4)

98.0 mg of Compound "f" obtained in Reference Example 6 was dissolved in 30 ml of methanol, and 1.0 ml of an ammonia/methanol solution (6.1M) was added to the solution. The reaction mixture was allowed to stand for 5 hours and 40 minutes at 25° C.

Then, the solvent was distilled off, and the resultant residue was purified by column chromatography (silica gel; chloroform:methanol=from 10:1 to 5:1) to obtain violet fractions. After the solvent was distilled off, the resultant residue was dissolved in a small amount of methanol/dichloromethane solution. n-Hexane was added to the solution to give a powder, which was collected by filtration and dried in Xvacuo to give 64.8 mg (yield 76%) of Compound 4 as a grayish green powder.

TLC: Rf=0.37 (chloroform:methanol=4:1)

FAB-MS(m/z): 321(M+ +1); $C_{14}H_{16}N_4O_5$: 320

IR (cm$^{-1}$): 3420, 3350, 2960, 2920, 1715, 1600, 1550, 1540, 1340, 1080, 1000

$^1$H-NMR: δ, ppm(270 MHz, pyridine-d$_5$) 2.12(s, 3H), 2.23(dd, J=2.0 and 4.8 Hz, 1H), 2.48(d, J=4.8 Hz, 1H), 3.69(dd, J=1.8 and 13.0 Hz, 1H), 4.30(dd, J=3.5 and 10.8 Hz, 1H), 4.50(d, J=12.8 Hz, 1H), 5.27(t, J=10.4 Hz, 1H), 5.58 (dd, J=3.4 and 10.5 Hz, 1H), 5.77(s, 1H), 7.3~8.0(bs, 4H), 8.3~8.6(bs, 1H)

EXAMPLE 5

Synthesis of 6-demethylmitomycin F (Compound 5)

152.2 mg of Compound 1 obtained in Example 1 was dissolved in 10 ml of acetone, and 50 mg of potassium carbonate and 1.0 ml of methyl iodide were added to the solution. The reaction mixture was stirred for 28 hours and 30 minutes at 25° C.

The solvent was distilled off under reduced pressure, and the resultant residue was purified by column chromatography (silica gel; chloroform:methanol=40:1) to obtain reddish violet fractions. After the solvent was distilled off, the resultant residue was dissolved again in a small amount of chloroform, and n-hexane was added to the solution to give a powder. The solvent was distilled off and dried in vacuo to give 110.8 mg (yield 70%) of Compound 5 as a reddish violet powder.

TLC: Rf=0.41 (chloroform:methanol=9:1)

FAB-MS(m/z): 350(M+ +1); $C_{16}H_{19}N_3O_6$: 349

IR (cm$^{-1}$): 3450, 3360, 3200, 2950, 1720, 1710, 1660, 1650, 1570, 1450, 1340, 1310, 1080, 1040, 950

$^1$H-NMR: δ, ppm(270 MHz, pyridine-d$_5$) 2.17(d, J=2.2 and 4.6 Hz, 1H), 2.25(s, 3H), 2.55(d, J=4.6 Hz, 1H), 3.20(s, 3H), 3.48(dd, J=2.1 and 12.5 Hz, 1H), 3.60(s, 3H), 3.99(dd, J=4.3 and 11.3 Hz, 1H), 4.22(d, J=12.6 Hz, 1H,), 4.80(bt, J=11 Hz, 1H), 5.35(dd, J=4.4 and 10.4 Hz, 1H), 5.71(s, 1H), 7.4~8.0(bs, 2H)

EXAMPLE 6

Synthesis of 6-demethylporfiromycin (Compound 6)

123.3 mg of Compound 3 obtained in Example 3 was dissolved in 10 ml of anhydrous N,N-dimethylformamide, and 50 mg of potassium carbonate and 1.0 ml of methyl iodide were added to the solution. The reaction mixture was stirred for 4 hours and 30 minutes at 25° C.

The resultant reaction mixture was diluted with a chloroform. After the inorganic salt was removed by filtration, the solvent was distilled off under reduced pressure. The residue obtained was purified by column chromatography (silica gel; chloroform:methanol= from 40:1 to 20:1) to obtain violet fractions.

Fractions thus obtained were treated in a similar manner to that described in Example 5 to give 99.6 mg (yield 77%) of Compound 6 as a violet powder.

TLC: Rf=0.23 (chloroform:methanol=9:1)

FAB-MS(m/z): 335(M+ +1); $C_{15}H_{18}N_4O_5$: 334

IR (cm$^{-1}$): 3420, 3320, 3200, 2950, 1710, 1600, 1550, 1450, 1330, 1260, 1080, 950

$^1$H-NMR: δ, ppm(270 MHz, pyridine-d$_5$) 2.15(dd, J=2.0 and 4.8 Hz, 1H), 2.24(s, 3H), 2.54(d, J=4.6 Hz, 1), 3.18(s, 3H), 3.53(dd, J=2.0 and 12.8 Hz, 1H), 4.02(dd, J=4.3 and 11.5 Hz, 1H), 4.53(d, J=12.8 Hz, 1H), 4.82(bt, J=11Hz, 1H), 5.40(dd, J=4.3 and 10.4 Hz, 1H), 5.79(s, 1H), 7.4~8.1(bs, 4H)

EXAMPLE 7

Synthesis of 6-chloro-6-demethylmitomycin C (Compound 7)

23.6 mg of Compound "h" obtained in Reference Example 8 was dissolved in 2.0 ml of an ammonia/methanol solution (6.1N), and 20 mg of dimedone was added to the solution. The reaction mixture was allowed to stand for 3 hours and 20 minutes at 25° C.

The resultant reaction mixture was diluted with a saturated saline solution and extracted with chloroform several times, and the solution was dried. After the desiccant was removed by filtration, the solvent was distilled off, and the resultant residue was purified by preparative TLC(silica gel; chloroform:methanol=6:1) to give a bluish violet zone. The zone was scraped off and extracted with a chloroform/methanol solution, and the solvent was distilled off.

The residue was dissolved in a small amount of chloroform, and n-hexane was added to the solution to give a powder. The solvent was distilled off and dried in vacuo, to give 3.5 mg (yield 19%) of Compound 7. The compound was dissolved in chloroform, and the solution was allowed to stand to give bluish violet needles.
TLC: Rf=0.20 (chloroform:methanol=9:1)
FAB-MS(m/z): 355, 357(2:1) (M$^+$+1); $C_{14}H_{15}{}^{35}ClN_4O_5$: 354
IR (cm$^{-1}$): 3430, 3300, 3200, 2930, 1710, 1600, 1560, 1550, 1460, 1420, 1340, 1330, 1070, 950
$^1$H-NMR: δ, ppm(90 MHz, pyridine-d$_5$) 2.1(bs, 1H), 2.73(m, 1H), 3.11(d, J=5Hz, 1H), 3.22(s, 3H), 3.57(dd, J=2 and 13 Hz, 1H), 3.96(dd, J=5 and 12 Hz, 1H), 4.48(d, J=14 Hz, 1H), 4.99(bt, J=11 Hz, 1H), 5.33(dd, J=5 and 11 Hz, 1H), 7.3~7.7(bs, 2H), 8.2~8.8(bs, 2H)

EXAMPLE 8

Synthesis of 6-bromo-6-demethylmitomycin C
(Compound 8)

118.9 mg of Compound "i" obtained in Reference Example 9 was dissolved in 10 ml of an ammonia/methanol solution (6.1N), and 90 mg of dimedone was added to the solution. The reaction mixture was stirred for 3 hours and 30 minutes at 25° C.

The resultant reaction mixture was diluted with a saturated saline solution and it was extracted with chloroform several times. The solution obtained was dried over anhydrous sodium sulfate, and the desiccant was removed by filtration. After the solvent was distilled off, the resultant residue was purified by column chromatography (silica gel; chloroform:methanol=from 20:1 to 10:1) to obtain bluish violet fractions.

The solvent of the fractions was distilled off and the resultant residue was dissolved in dichloromethane. The solution was allowed to stand to give 46.3 mg of Compound 8 (yield 55%) as bluish violet needles.
TLC: Rf=0.20 (chloroform:methanol=9:1)
FAB-MS(m/z): 399, 401(1:1) (M$^+$+1); $C_{14}H_{15}{}^{79}BrN_4O_5$: 398
IR (cm$^{-1}$): 3450, 3400, 3280, 3000, 2950, 1710, 1600, 1560, 1550, 1450, 1410, 1330, 1070, 950
$^1$H-NMR: δ, ppm(270 MHz, pyridine-d$_5$) 2.18(bs, 1H), 2.75(bs, 1H), 3.14(bs, 1H), 3.22(s, 3H), 3.59(bd, J=12 Hz, 1H), 4.01(dd, J=4.2 and 11.2 Hz, 1H), 4.51(d, J=12.8 Hz, 1H), 5.09(bt, J=11 Hz, 1H), 5.37(dd, J=4.3 and 10.5 Hz, 1H), 7.4~7.9(bs, 2H), 8.5~8.8(bs, 2H)

EXAMPLE 9

Synthesis of 6-bromo-6-demethylmitomycin D
(Compound 9)

203 mg of Compound "c" obtained in Reference Example 3 was dissolved in 10 ml of methanol, and 106 mg of dimedone and 1.0 ml of an ammonia/methanol solution (6.1M) were added to the solution. The reaction mixture was allowed to stand for 17 hours at ambient temperature. To the solution, 1.0 ml of an ammonia/methanol solution and 50 mg of dimedone were added and the solution was allowed to stand for 3 hours and 30 minutes at ambient temperature.

The solvent of the reaction mixture was distilled off, and the residue obtained was purified by column chromatography (silica gel; chloroform:methanol=from 20:1 to 10:1) to give violet fractions.

The solvent of the fractions was distilled off, and the residue was crystallized from ethanol to give 83.5 mg (yield 54%) of Compound 9 as violet prisms.
TLC: Rf=0.21 (chloroform:methanol=9:1)
EI-MS(m/z): 398, 400(M$^+$+1); $C_{14}H_{15}{}^{79}BrN_4O_5$: 398
IR (cm$^{-1}$): 3410, 3290, 2950, 1720, 1590, 1560, 1540, 1450, 1420, 1340, 1070
$^1$H-NMR: δ, ppm(270 MHz, pyridine-d$_5$) 2.13(s, 3H), 2.23(dd, J=1.8 and 4.8 Hz, 1H), 2.47(d, J=4.8 Hz, 1H), 3.65(dd, J=2.0 and 13.0 Hz, 1H), 4.22(dd, J=3.4 and 9.8 Hz, 1H), 4.40(d, J=13.0 Hz, 1H), 5.21(t, J=10.3 Hz, 1H), 5.41(dd, J=3.5 and 10.6 Hz, 1H), 7.2~7.7(br, 2H), 8.3~8.6(br, 3H)

EXAMPLE 10

Synthesis of 6-chloro-6-demethylmitomycin A
(Compound 10)

92.5 mg of Compound "g" obtained in Reference Example 7 was dissolved in 10 ml of anhydrous methanol, and 23 mg of dimedone and 31 mg of potassium carbonate were added to the solution. The resultant solution was stirred for 30 minutes at ambient temperature.

The resultant reaction mixture was diluted with a phosphate buffer (pH4) and extracted with chloroform. The extract was washed with a saturated saline solution, and dried over anhydrous sodium sulfate. After the solvent was distilled off, the resultant residue was dried thoroughly in vacuo to give 93.7 mg of a crude product of Compound "h" which also could been obtained in Reference Example 8.

83.7 mg of the crude product of Compound "h" (89.3% of the total weight obtained above) was dissolved in 10 ml of anhydrous methanol, and 30 mg of potassium carbonate was added to the solution. The reaction mixture was stirred for 42 hours at ambient temperature. In 12 hours and in 35 hours from the beginning of the reaction, 15 mg of potassium carbonate was added twice.

The resultant reaction mixture was treated in a similar manner to that described above. The residue obtained was purified by preparative TLC(silica gel; chloroform:methanol=9:1) to obtain a brown zone. The zone was scraped off and extracted with a chloroform/methanol solution, and the solvent was distilled off.

The residue obtained was dissolved again in chloroform, and silica gel was added for adsorption. The mixture was allowed to stand for 2 hours at ambient temperature. Silica gel was extracted with the solution (chloroform:methanol=9:1), and the solvent was distilled off.

The residue thus obtained was treated in a similar manner to that described in Example 7 to give 5.9 mg (yield 12%) of Compound 10 as a violet powder.
TLC: Rf=0.36 (chloroform:methanol=9:1)
FAB-MAS(m/z): 370, 372(M$^+$+1); $C_{15}H_{16}{}^{35}ClN_3O_6$: 369
IR (cm$^{-1}$): 3500, 3200, 2900, 1720, 1710, 1670, 1630, 1560, 1450, 1410, 1340, 1260, 1070

$^1$H-NMR: δ, ppm(270 MHz, pyridine-$d_5$) 2.0~2.5(br, 1H), 2.78(bs, 1H), 3.14 (bs, 1H), 3.23(s, 3H), 3.55(bd, J=12.4 Hz, 1H), 3.98(dd, J=4.5 and 10.9 Hz, 1H), 4.18(s, 3H), 4.20(d, J=12.4 Hz, 1H), 4.9~5.2(1H, overlapped with a signal from H$_2$O), 5.34(dd, J=4.5 and 10.4 Hz, 1H), 7.3~8.0(br, 2H)

EXAMPLE 11

Synthesis of 6-bromo-6-demethylmitomycin A (Compound 11)

111.7 mg of Compound "i" obtained in Reference Example 9 was dissolved in 10 ml of anhydrous methanol, and 28 mg of dimedone and 41 mg of potassium carbonate were added to the solution. The resultant reaction mixture was stirred for 20 minutes at ambient temperature.

The resultant reaction mixture was diluted with a phosphate buffer (pH4) and extracted with chloroform. The extract was washed with a saturated saline solution, and dried over anhydrous sodium sulfate. After the solvent was distilled off, the resultant residue was dried thoroughly in vacuo to give 89.4 mg of a crude product of Compound "k" which also could been obtained in Reference Example 11.

81.8 mg of the crude product of Compound "k" (91.5% of the total weight obtained above) was dissolved in 10 ml of anhydrous methanol, and 10 mg of potassium carbonate was added to the solution. The reaction mixture was stirred for 24 hours and 10 minutes at ambient temperature. In 1 hour, in 5 hours and in 18 hours from the beginning of the reaction, 14 mg of potassium carbonate was added to the reaction mixture three times.

The resultant reaction mixture was treated in a similar manner to that described above. The residue obtained was purified by preparative TLC(silica gel; chloroform:methanol=9:1) to obtain a brown zone. The zone was extracted and concentrated in a similar manner to that described in Example 10.

The resultant residue was dissolved in chloroform and to the solution was added silica gel for adsorption. The reaction mixture was allowed to stand for 2 hours and 20 minutes at ambient temperature.

The resultant reaction mixture was treated in a similar manner to that described in Example 10 to give 29.9 mg (yield 40%) of Compound 11 as a violet powder.

TLC: Rf=0.38 (chloroform:methanol=9:1)

FAB-MAS(m/z): 414, 416(M$^+$+1); C$_{15}$H$_{16}$$^{79}$BrN$_3$O$_6$: 413

IR (cm$^{-1}$): 3450, 3300, 3200, 2950, 1720, 1710, 1660, 1630, 1560, 1550, 1460, 1450, 1410, 1340, 1250, 1070

$^1$H-NMR: δ, ppm(270 MHz, pyridine-$d_5$) 2.20(bs, 1H), 2.76(bs, 1H), 3.13(bs, 1H), 3.23(s, 3H), 3.54(bd, J=12 Hz, 1H), 3.98(dd, J=4.4 and 10.8 Hz, 1H), 4.19(s, 3H), 4.21(d, J=12.4 Hz, 1H), 5.12(bt, J=ca. 10 Hz, 1H), 5.34(dd, J=4.5 and 10.4 Hz, 1H), 7.3~7.9(br, 2H)

EXAMPLE 12

Synthesis of 6-bromo-6-demethylmitomycin B (Compound 12)

55.1 mg of Compound "n" obtained in Reference Example 13 was dissolved in 5.0 ml of anhydrous methanol, and 14 mg of dimedone and 27 mg of potassium carbonate were added to the solution. The reaction mixture was stirred for 46 hours at ambient temperature.

After the solvent was distilled off from the reaction mixture, the residue was purified by preparative TLC(silica gel; chloroform:methanol=9:1) to obtain a light brownish zone. The zone was extracted and concentrated in a similar manner to that described in Example 10.

The resultant residue was dissolved again in chloroform and to the solution was added silica gel for adsorption, and the reaction mixture was allowed to stand for 3 hours at ambient temperature.

The resultant reaction mixture was treated in a similar manner to that described in Example 10 to give 10.9 mg (yield 25%) of Compound 12 as a violet powder.

TLC: Rf=0.42 (chloroform:methanol=9:1)

FAB-MAS(m/z): 414, 416(M$^+$+1); C$_{15}$H$_{16}$$^{79}$BrN$_3$O$_6$: 413

IR (cm$^{-1}$): 3460, 3400, 3300, 3200, 2950, 1710, 1660, 1630, 1620, 1560, 1550, 1450, 1410, 1340, 1250, 1070

$^1$H-NMR: δ, ppm(270 MHz, pyridine-$d_5$) 2.13(s, 3H), 2.24(dd, J=2.0 and 4.5 Hz, 1H), 2.48(d, J=5.0 Hz, 1H), 3.57(bd, J=12.4 Hz, 1H), 4.13(d, J=12.4 Hz, 1H), 4.15(s, 3H), 4.20(dd, J=3.5 and 9.4 Hz, 1H), 5.16(bt, J=10.1 Hz, 1H), 5.40(dd, J=3.5 and 10.4 Hz, 1H), 7.4~7.8(br, 3H)

EXAMPLE 13

Synthesis of 7-deamino-6-demethyl-7-(N-ethylenimino)mitomycin C (Compound 13)

52 mg of 6-demethylmitomycin A was dissolved in 5.0 ml of methanol and excessive amount of an aqueous solution of ethylenimine was added. The reaction mixture was stirred for 30 minutes at ambient temperature.

The solvent was distilled off under reduced pressure, and the resultant residue was purified by preparative TLC(silica gel; chloroform:methanol=9:1), and treated in a similar manner to that described in Example 7 to give 1.4 mg (yield 2.6%) of Compound 13 as a violet powder.

TLC: Rf=0.25 (chloroform:methanol=9:1)

FAB-MS(m/z): 347(M$^+$+1)C$_{16}$H$_{18}$N$_4$O$_5$: 346

IR (cm$^{-1}$): 3420, 3300, 3200, 2920, 1720, 1710, 1640, 1570, 1550, 1470, 1450, 1340, 1260, 1070

$^1$H-NMR: δ, ppm(270 MHz, pyridine-$d_5$) 2.10(s, 4H), 2.74(m, 1H), 3.12(m, 1H), 3.19(s, 3H), 3.54(bd, J=12.4 Hz, 1H), 3.98(dd, J=4.0 and 10.9 Hz, 1H), 4.29(d, J=12.4 Hz, 1H), 5.02(bt, J=ca. 10 Hz, 1H), 5.37(dd, J=4.0 and 9.9 Hz, 1H), 5.81(s, 1H), 7.3~7.8(br, 2H)

Reference Examples are mentioned below, and the structures of the Compounds are shown in Table 5.

TABLE 5

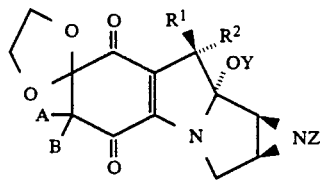

| Compound (Reference Example) | A | B | Y | Z | R¹ | R² |
|---|---|---|---|---|---|---|
| a (1) | =CH$_2$ | | CH$_3$ | COCH$_3$ | CH$_2$OCONH$_2$ | H |
| b (2) | H | PhSe | CH$_3$ | COCH$_3$ | CH$_2$OCONH$_2$ | H |
| c (3) | =CH$_2$ | | H | CH$_3$ | H | CH$_2$OCONH$_2$ |
| d (4) | H | PhSe | H | CH$_3$ | H | CH$_2$OCONH$_2$ |
| e (5) | H | H | CH$_3$ | COCH$_3$ | CH$_2$OCONH$_2$ | H |
| f (6) | H | H | H | CH$_3$ | H | CH$_2$OCONH$_2$ |
| g (7) | Cl | PhSe | CH$_3$ | COCH$_3$ | CH$_2$OCONH$_2$ | H |
| h (8) | Cl | H | CH$_3$ | COCH$_3$ | CH$_2$OCONH$_2$ | H |
| i (9) | Br | Br | CH$_3$ | COCH$_3$ | CH$_2$OCONH$_2$ | H |
| j (10) | Br | PhSe | CH$_3$ | COCH$_3$ | CH$_2$OCONH$_2$ | H |
| k (11) | Br | H | CH$_3$ | COCH$_3$ | CH$_2$OCONH$_2$ | H |
| m (12) | Cl | Cl | CH$_3$ | COCH$_3$ | CH$_2$OCONH$_2$ | H |
| n (13) | Br | Br | H | CH$_3$ | H | CH$_2$OCONH$_2$ |

REFERENCE EXAMPLE 1

1a-Acetyl-7-demethoxy-6-demethyl-6,7-dihydro-7-ethylenedioxy-6-methylenemitomycin A (Compound "a")

5.77 g of 1a-Acetyl-7-demethoxy-6,7-dihydro-7-ethylenedioxy-6-phenylselenomitomycin A (JP-A-70490/89.) was dissolved in 100 ml of dichloromethane and to the solution was added 2.82 g of potassium carbonate. To the reaction mixture was added 50 ml of a dichloromethane solution containing 2.59 g of m-chloroperbenzoic acid (purity ca. 80%) dropwise over a period of 15 minutes while stirring at −40° C. The reaction mixture was stirred at −40° to −30° C. for 40 minutes, and subsequently at 20° C. for 50 minutes.

The resultant reaction mixture was washed with 1:1 mixed solution of a sodium thiosulfate (M/10) solution and a saturated sodium bicarbonate solution and washed with a saturated saline solution. The solution was dried over anhydrous sodium sulfate. After the desiccant was removed by filtration, the solvent was concentrated under reduced pressure, and n-hexane was added to the concentrated solution to give a powder. The powder obtained was collected by filtration and dried in vacuo to give 3.77 (yield 90%) of Compound "a".

The purity of Compound "a" thus obtained was ca. 90% from $^1$H-NMR spectroscopy.

TLC: Rf=0.42 (chloroform:acetonitrile:n-hexane=5:5:1)

FAB-MS(m/z): 420(M$^+$ +1); C$_{19}$H$_{21}$N$_3$O$_8$: 419

IR (cm$^{-1}$): 3450, 3370, 3200, 3070, 2930, 2900, 1720, 1710, 1690, 1660, 1570, 1460, 1450, 1390, 1340, 1270, 1180, 1070, 1030

$^1$H-NMR: δ, ppm(400 MHz, chloroform-d$_1$/pyridine-d$_5$) 2.08(s, 3H), 3.17(s, 3H), 3.24(dd, J=4.4 and 2.0 Hz, 1H), 3.50 (d, J=4.4 Hz, 1H), 3.48(dd, J=13.3 and 2.0 Hz, 1H), 3.79(dd, J=11.1 and 4.9 Hz, 1H), 4.17(t, J=10.8 Hz, 1H), 4.04~4.29(m, 4H), 4.38(d, J=13.3 Hz, 1H), 5.04(dd, J=10.8 and 4.7 Hz, 1H), 5.79(bs, 2H), 6.09(bs, 1H), 6.36(bs, 1H)

REFERENCE EXAMPLE 2

1a-Acetyl-7-demethoxy-6-demethyl-6,7-dihydro-7-ethylenedioxy-6-phenylselenomitomycin A (Compound "b")

421 mg of Compound "a" obtained in Reference Example 1 was dissolved in 25 ml of anhydrous tetrahydrofuran, and 238 mg of morpholinophenylselenenamide was added to the solution. The reaction mixture was stirred for 3 hours at 25° C.

The resultant reaction mixture was purified by column chromatography (silica gel; chloroform:methanol=30:1) to give yellow fractions. Fractions thus obtained were treated in a similar manner to that described in Example 5 to give 318 mg (yield 56%) of Compound "b" as a yellow powder.

From the $^1$H-NMR spectral analysis, it was found that Compound "b" was an equilibrated mixture of diastereoisomers which were different in stereochemistry at the 6th-position.

TLC: Rf=0.30 (chloroform:acetonitrile:n-hexane=5:5:1)

FAB-MS(m/z): 562, 564(M$^+$ +1); C$_{24}$H$_{25}$N$_3$O$_8$$^{78}$Se: 561

IR (cm$^{-1}$): 3470, 3370, 3060, 2960, 2900, 1700, 1660, 1570, 1460, 1400, 1340, 1250, 1080, 1030

$^1$H-NMR: δ, ppm(400 MHz, chloroform-d$_1$) Major isomer: 2.20(s, 3H), 3.21(s, 3H), 3.26(dd, J=2.0 and 4.7 Hz, 1H), 3.41(dd, J=2.0 and 13.0 Hz, 1H), 3.52(d, J=4.7 Hz, 1H), 3.73(dd, J=4.9 and 10.8 Hz, 1H), 3.84(d, J=13.0 Hz, 1H), 4.02(s, 1H), 4.19(t, J=11 Hz, 1H), 4.01~4.20(m, 3H), 4.41(m, 1H), 4.91(bs, 2H), 4.95(dd, J=4.9 and 11.1 Hz, 1H), 7.28~7.38(m, 3H), 7.61(m, 2H) Minor isomer: 2.10(s, 3H), 3.21(s, 3H), 3.23(dd, J=2.0 and 4.4 Hz, 1H), 3.39(dd, J=2.0 and 13.0 Hz, 1H), 3.48(d, J=4.4 Hz, 1H), 3.67(dd, J=4.7 and 10.8 Hz, 1H), 4.17(s, 1H), 4.01~4.20(m, 4H), 4.31(m, 1H), 4.40(d, J=13.0 Hz, 1H), 4.81(dd, J=4.7 and 10.8 Hz, 1H), 4.89(bs, 2H), 7.28~7.38(m, 3H), 7.61(m, 2H)

REFERENCE EXAMPLE 3

7-Demethoxy-6-demethyl-6,7-dihydro-7-ethylenedioxy-6-methylenemitomycin B (Compound "c")

1.25 g of 7-Demethoxy-6,7-dihydro-7-ethylenedioxy-6-phenylselenomitomycin B (JP-A-70490/89) was dissolved in 25 ml of a dichloromethane, and 650 mg of potassium carbonate was added to the reaction mixture. 15 ml of a dichloromethane solution containing 630 mg of m-chloroperbenzoic acid (purity ca. 80%) was added dropwise to the reaction mixture over a period of 15 minutes while stirring at −40° C. The reaction mixture was stirred for 35 minutes at −30° C. and subsequently at 20° C. for 40 minutes.

The resultant reaction mixture was filtered with Celite (a filter aid; diatomaceous earth), and the resulting filtrate was concentrated under reduced pressure. n-Hexane was added to the residue to give a powder. The powder obtained was collected by filtration, and dried in vacuo to give 1.05 g of a crude product of Compound "c" as a yellow powder.

$^1$H-NMR: $\delta$, ppm(90 MHz, chloroform-$d_1$) (main peaks): 2.21(s, 3H), 6.03(bs, 1H), 6.31(bs, 1H)

REFERENCE EXAMPLE 4

7-Demethoxy-6-demethyl-6,7-dihydro-7-ethylenedioxy-6-phenylselenomitomycin B (Compound "d")

1.08 g of 7-Demethoxy-6,7-dihydro-7-ethylenedioxy-6-phenylselenomitomycin B (JP-A-70490/89) was dissolved in 20 ml of chloroform, and 560 mg of potassium carbonate was added to the solution and the mixture was stirred at −40° C. 10 ml of a dichloromethane solution containing 700 mg of m-chloroperbenzoic acid (purity ca. 80%) was added dropwise to the reaction mixture over a period of 20 minutes. The reaction mixture was stirred for 1 hour at −40° C. and for 40 minutes at a temperature from 0° C. to ambient temperature.

The resultant reaction mixture was cooled to 0° C., and 16 ml of a n-hexane solution containing N-benzyl-N-methylaminophenylselenenamide (ca. 0.1M) was dropwise added to the reaction mixture over a period of 30 minutes. The reaction mixture was stirred for 50 minutes.

The resultant reaction mixture was washed with a saturated saline solution, and dried over anhydrous sodium sulfate. The desiccant was removed by filtration, and the solvent was distilled off. The residue obtained was purified by column chromatography (silica gel; chloroform:methanol=20:1) to give yellow fractions.

Fractions thus obtained were treated in a similar manner to that described in Example 5 to give 240 mg (yield 23%) of Compound "d" as a yellow powder.

From the $^1$H-NMR spectral analysis, it was found that Compound "d" was an equilibrated mixture of diastereoisomers which were different in stereochemistry at the 6th-position.

TLC: Rf=0.46 (chloroform:methanol=9:1) Rf=0.30 (chloroform:acetonitrile:n-hexane=5:5:1)

FAB-MS(m/z): 520, 522(M$^+$+1); $C_{22}H_{23}N_3O_7{}^{78}Se$: 519

IR (cm$^{-1}$): 3420, 2950, 2900, 1700, 1640, 1560, 1460, 1340, 1240, 1210, 1100, 1030

$^1$H-NMR: $\delta$, ppm(90 MHz, pyridine-$d_5$) Major isomer: 2.1~2.3(m, 1H), 2.17(s, 3H), 2.46 (d, J=4.8 Hz, 1H), 3.42(dd, J=1.8 and 12.5 Hz, 1H), 3.54(d, J=12.3 Hz, 1H), 3.7~4.4(m, 5H), 4.07(s, 1H), 5.23(bt, J=10 Hz, 1H), 5.44(dd, J=3.3 and 10.4 Hz, 1H), 7.2~7.4(m, 3H), 7.3~7.6(bs, 2H), 7.7~7.9(m, 2H), 8.3~8.5(bs, 1H) Minor isomer (main peaks): 2.06(s, 3H), 3.50(dd, J=2.2 and 10 Hz, 1H), 5.25(bt, J=10 Hz, 1H), 5.48(dd, J=3.3 and 10 Hz, 1H), 7.3~7.6(bs, 2H), 8.3~8.5(bs, 1H)

REFERENCE EXAMPLE 5

1a-Acetyl-7-demethoxy-6-demethyl-6,7-dihydro-7-ethylenedioxymitomycin A (Compound "e")

180 mg of Compound "b" obtained in Reference Example 2 was dissolved in 30 ml of anhydrous benzene, and 0.85 ml of tributyltin hydride and 100 $\mu$l of triethylborane (1.0M; n-hexane solution) were added to the solution under an argon atmosphere. The reaction mixture was stirred at 25° C. In 15 minutes and in 1 hour from the beginning of the reaction, 100 $\mu$l each of the triethylborane solution was added to the solution, and stirred for 1 hour and 15 minutes from the beginning of the reaction.

A white precipitate formed during the reaction was collected by filtration. The filtrate was diluted with a chloroform and washed with a saturated sodium bicarbonate solution and a saturated saline solution successively. The resultant solution was dried over anhydrous sodium sulfate. After the desiccant was removed by filtration, the residue was purified by column chromatography (silica gel; chloroform:methanol=20:1) to obtain yellowish pink fractions. Fractions thus obtained were combined with white precipitate obtained above and treated in a similar manner to that described in Example 5 to give 127.2 mg (yield 97%) of Compound "e" as a yellowish pink powder.

TLC: Rf=0.22 (n-hexane:acetonitrile:-chloroform=1:5:5)

FAB-MS(m/z): 408(M$^+$+1); $C_{18}H_{21}N_3O_8$: 407

IR (cm$^{-1}$): 3450, 2920, 1700, 1650, 1570, 1460, 1390, 1340, 1260, 1190, 1150, 1070, 1020

$^1$H-NMR: $\delta$, ppm(270 MHz, pyridine-$d_5$) 2.08(s, 3H), 3.11(s, 3H), 3.25(d, J=16.1 Hz, 1H), 3.46(dd, J=1.9 and 4.5 Hz, 1H), 3.51(dd, J=1.9 and 13.1 Hz, 1H), 3.56(d, J=16.3 Hz, 1H), 3.79(d, J=4.4 Hz, 1H), 3.92~4.05(m, 2H), 4.08~4.18(m, 2H), 4.28~4.37(m, 1H), 4.31(d, J=12.8 Hz, 1H), 4.60(t, J=11.0 Hz, 1H), 5.72(dd, J=4.6 and 10.8 Hz, 1H), 7.4~7.9(bs, 2H)

REFERENCE EXAMPLE 6

7-Demethoxy-6-demethyl-6,7-dihydro-7-ethylenedioxymitomycin B (Compound "f")

283 mg of Compound "d" obtained in Reference Example 4 was dissolved in anhydrous benzene 40 ml under an argon atmosphere. 1.40 ml of tributyltin hydride and 0.50 ml of triethylborane in 1.0M hexane solution were added to the solution. The reaction mixture was stirred at 25° C. In 1 hour and in 1 hour and 35 minutes from the beginning of the reaction, 0.30 ml of a triethylborane solution was added twice to the reaction mixture. In 1 hour and 20 minutes from the beginning of the reaction, 0.70 ml of tributyltin hydride was added the solution. The reaction mixture was stirred for 13 hours from the beginning of the reaction.

The solvent of the reaction mixture was distilled off under reduced pressure, and the white precipitate formed was collected by filtration. The precipitate was washed with n-hexane and dried over in vacuo to give 167.8 mg (yield 91%) of Compound "f" as a white powder.

TLC: Rf=0.37 (chloroform:methanol=9:1)
FAB-MS(m/z): 366(M+ +1); $C_{16}H_{19}N_3O_7$: 365
IR (cm$^{-1}$): 3480, 3370, 3320, 3200, 3050, 2970, 2900, 1730, 1710, 1640, 1570, 1480, 1460, 1330, 1020

$^1$H-NMR: δ, ppm(270 MHz, pyridine-d$_5$) 2.10(s, 3H), 2.20(dd, J=1.8 and 4.8 Hz, 1H), 2.46(d, J=4.6 Hz, 1H), 3.08(d, J=16.1 Hz, 1H), 3.33(d, J=16.1 Hz, 1H), 3.53(dd, J=1.9 and 12.5 Hz, 1H), 3.8~4.0(m, 4H), 4.25~4.35(m, 1H), 4.29(dd, J=3.3 and 9.7 Hz, 1H), 5.21(bt, J=10 Hz, 1H), 5.44(dd, J=3.4 and 10.5 Hz, 1H), 7.2~7.6(bs, 2H), 8.30(s, 1H)

REFERENCE EXAMPLE 7

1a-Acetyl-6-chloro-7-demethoxy-6-demethyl-6,7-dihydro-7-ethylenedioxy-6-phenylselenomitomycin A (Compound "g")

133 mg of Compound "b" obtained in Reference Example 2 was dissolved in 2.5 ml of dichloromethane, and 60 mg of sodium bicarbonate and 62 mg of N-chlorosuccinimide were added to the solution. The reaction mixture was stirred for 22 hours at 25° C.

A phosphate buffer (1.0M; pH7) was added to the reaction mixture. After the solution was stirred for a while, the resultant solution was extracted with chloroform. The chloroform solution was washed twice with a saturated saline solution, and dried over anhydrous sodium sulfate. After the desiccant was removed by filtration, the solvent was distilled off. The residue obtained was purified by column chromatography (silica gel; chloroform:methanol=30:1) to obtain yellow fractions. The fractions thus obtained were treated in a similar manner to that described in Example 5 to give 42.9 mg (yield 30%) of Compound "g" as a yellow powder.

From the $^1$H-NMR spectral analysis, it was found that Compound "g" was an equilibrated mixture of diastereoisomers which were different in stereochemistry at the 6th-position.

TLC: Rf=0.51 and 0.45 (chloroform:acetonitrile:n-hexane=5:5:1)

FAB-MS(m/z): 596, 598, 600(1:2:1)(M+ +1); $C_{24}H_{24}{}^{35}ClN_3O_8{}^{78}Se$: 595

$^1$H-NMR: δ, ppm(270 MHz, pyridine-d$_5$) Major isomer: 2.34(s, 3H), 3.10(s, 3H), 3.3~3.5(m, 2H), 3.66(bd, J=13 Hz, 1H), 3.75~4.8(m, 7H), 5.81(dd, J=4.7 and 11.1 Hz, 1H), 7.2~8.0(m, 7H) Minor isomer (main peaks): 2.00(s, 3H), 3.33(s, 3H), 5.56(dd, J=4.6 and 10.6 Hz, 1H)

REFERENCE EXAMPLE 8

1a-Acetyl-6-chloro-7-demethoxy-6-demethyl-6,7-dihydro-7-ethylenedioxymitomycin A (Compound "h")

35.5 mg of Compound "g" obtained in Reference Example 7 (purity ca. 50%) was dissolved in 5.0 ml of anhydrous benzene. 15 μl of tributyltin hydride was added to the solution. The reaction mixture was stirred under an argon atmosphere for 1 hour and 15 minutes at 25° C. and subsequently at 45° C. for 1 hour and 45 minutes. After 15 μl of tributyltin hydride was added to the reaction mixture, and the mixture was stirred and heated under reflux for 1 hour.

The resultant reaction mixture was diluted with chloroform, and the diluted mixture was washed twice with a saturated saline solution and dried over anhydrous sodium sulfate. The desiccant was removed by filtration, and the solvent was distilled off. The residue thus obtained was purified by preparative TLC (silica gel; chloroform:acetonitrile:n-hexane=5:5:1), and treated in a similar manner to that described in Example 7 to give 4.8 mg (yield ca. 40%) of Compound "h" as a yellow powder.

From the $^1$H-NMR spectral analysis, it was found that Compound "h" was an equilibrated mixture of diastereoisomers which were different in stereochemistry at the 6th-position.

TLC: Rf=0.40 (chloroform:methanol=9:1) Rf=0.33 (chloroform:acetonitrile:n-hexane=5:5:1)

FAB-MS(m/z): 442, 444(2:1)(M+ +1); $C_{18}H_{20}{}^{35}ClN_3O_8$: 441

IR (cm$^{-1}$): 3460, 3340, 3200, 3060, 2920, 1710, 1660, 1570, 1340, 1200, 1070, 1030, 960

$^1$H-NMR: δ, ppm(270 MHz, pyridine-d$_5$) Major isomer: 2.12(s, 3H), 3.12(s, 3H), 3.4~3.6(m, 1H), 3.54(bd, J=13 Hz, 1H), 3.8~4.6(m, 7H), 4.53(bt, J=11 Hz, 1H), 5.63(dd, J=4.6 and 10.8 Hz, 1H), 6.28(s, 1H), 7.4~7.8(bs, 2H) Minor isomer: 2.07(s, 3H), 3.12(s, 3H), 3.4~3.6(m, 2H), 3.8~4.6(m, 7H), 4.67(bt, J=11 Hz, 1H), 5.70(dd, J=5 and 11.0 Hz, 1H), 5.77(s, 1H), 7.4~7.8(bs, 2H)

REFERENCE EXAMPLE 9

1a-Acetyl-7-demethoxy-6-demethyl-6,6-dibromo-6,7-dihydro-7-ethylenedioxymitomycin A (Compound "i")

199.6 mg of Compound "a" obtained in Reference Example 1 was dissolved in 20 ml of anhydrous tetrahydrofuran and 100 μl of diethylamine and 171 mg of N-bromosuccinimide were added to the reaction mixture. The reaction mixture was stirred for 1 hour and 30 minutes at 25° C.

The resultant reaction mixture was washed with a saturated sodium bicarbonate solution, phosphate buffer (pH4), a saturated saline solution successively, and dried over anhydrous sodium sulfate. After the desiccant was removed by filtration, the solvent was distilled off. The residue obtained was purified by column chromatography (silica gel; chloroform:methanol=9:1) to obtain yellow fractions Fractions thus obtained were treated in a similar manner to that described in Example 5 to give 117.2 mg (yield 44%) of Compound "i" as a yellow powder.

TLC: Rf=0.35 (chloroform:acetonitrile:n-hexane=5:5:1)

FAB-MS(m/z): 564, 566, 568(1:2:1)(M+ +1); $C_{18}H_{19}{}^{79}Br_2N_3O_8$: 563

IR (cm$^{-1}$): 3450, 3360, 3200, 2940, 2900, 1720, 1710, 1700, 1670, 1580, 1340, 1280, 1200, 1070, 960

$^1$H-NMR: δ, ppm(270 MHz, pyridine-d$_5$) 2.08(s, 3H), 3.18(s, 3H), 3.4~3.6(m, 2H), 3.8~4.5(m, 7H), 4.72(bt, J=10.7 Hz, 1H), 5.73(dd, J=4.7 and 10.9 Hz, 1H), 7.5~7.8(bs, 2H)

REFERENCE EXAMPLE 10

1a-Acetyl-6-bromo-7-demethoxy-6-demethyl-6,7-dihydro-7-ethylenedioxy-6-phenylselenomitomycin A (Compound "j")

28.0 mg of Compound "b" obtained in Reference Example 2 was dissolved in 3.0 ml of dichloromethane. 14 mg of N-bromosuccinimide was added to the solution. The reaction mixture was stirred for 3 hours at 25° C. The resultant reaction mixture was diluted with a chloroform and washed twice with a saturated sodium bicarbonate solution and washed once with a saturated saline solution. The solution obtained was dried over anhydrous sodium sulfate. After the desiccant was removed by filtration, the solvent was distilled off. The residue was purified by column chromatography (silica gel; chloroform:methanol=20:1) to obtain yellow fractions.

Fractions thus obtained were treated in a similar manner to that described in Example 5 to give Compound "j" 20.8 mg (yield 70%) as a yellow powder.

From the $^1$H-NMR spectral analysis, it was found that Compound "j" was an equilibrated mixture of diastereoisomers which were different in stereochemistry at the 6th-position.

TLC: Rf=0.38 and 0.33 (chloroform:acetonitrile:n-hexane=5:5:1)

FAB-MS(m/z): 640, 642, 644(1:2:1)(M+ +1); $C_{24}H_{24}{}^{79}BrN_3O_8{}^{78}Se$: 639

$^1$H-NMR: δ, ppm(270 MHz, pyridine-d$_5$) Major isomer: 2.35(s, 3H), 3.09(s, 3H), 3.39(dd, J=2.0 and 13.0 Hz, 1H), 3.51(dd, J=1.8 and 4.6 Hz, 1H), 3.67(d, J=13.2 Hz, 1H), 3.85(d, J=4.6 Hz, 1H), 4.0∼4.7(m, 4H), 4.22(dd, J=4.5 and 11.1 Hz, 1H), 4.71(t, J=11.1 Hz, 1H), 5.81(dd, J=4.7 and 10.9 Hz, 1H), 7.3∼7.9(m, 5H), 7.5∼8.0(bs, 2H) Minor isomer: 1.99(s, 3H), 3.15(d, J=13.4 Hz, 1H), 3.31(s, 3H), 3.33(dd, J=1.8 and 12.6 Hz, 1H), 3.46(dd, J=1.8 and 4.6 Hz, 1H), 3.79(d, J=4.6 Hz, 1H), 4.0∼4.7(m, 5H), 4.64(t, J=10.8 Hz, 1H), 5.56(dd, J=4.6 and 10.6 Hz, 1H), 7.3∼7.9(m, 5H), 7.5∼8.0(bs, 2H)

REFERENCE EXAMPLE 11

1a-Acetyl-6-bromo-7-demethoxy-6-demethyl-6,7-dihydro-7-ethylenedioxymitomycin A (Compound "k")

18.9 mg of Compound "j" obtained in Reference Example 10 was dissolved in 3.0 ml of dichloromethane, and 8.5 μl of tributyltin hydride was added to the solution. The reaction mixture was stirred under an argon atmosphere for 1 hour and 40 minutes at 25° C., and stirred at 50° C. for 3 hours and 10 minutes. Then, 8.5 μl of tributyltin hydride was added to the reaction mixture, and the mixture was stirred for additional 2 hours.

After the solvent was distilled off under reduced pressure, the residue obtained was purified by preparative TLC (silica gel; chloroform:acetonitrile:n-hexane=5:5:1), and treated in a similar manner to that described in Example 7 to give 7.2 mg (yield 50%) of Compound "k" as a yellow powder.

From the $^1$H-NMR spectral analysis, it was found that Compound "k" was an equilibrated mixture of diastereoisomers which were different in stereochemistry at the 6th-position.

TLC: Rf=0.38 (chloroform:acetonitrile:n-hexane=5:5:1)

FAB-MS(m/z): 486, 488(1:1)(M+ +1); $C_{18}H_{20}{}^{79}BrN_3O_8$: 485

IR (cm$^{-1}$): 3460, 3340, 3200, 3060, 2920, 1710, 1610, 1570, 1340, 1200, 1070, 1030, 950

$^1$H-NMR: δ, ppm(270 MHz, pyridine-d$_5$) Major isomer: 2.07(s, 3H), 3.13(s, 3H), 3.4∼3.6(m, 2H), 3.8∼4.5(m, 7H), 4.55(bt, J=11 Hz, 1H), 5.65(dd, J=4.6 and 10.8 Hz, 1H), 6.34(s, 1H), 7.4∼7.9(bs, 2H) Minor isomer: 2.08(s, 3H), 3.14(s, 3H), 3.4∼3.6(m, 2H), 3.8∼4.5(m, 7H), 4.73(bt, J=11 Hz, 1H), 5.54(s, 1H), 5.78(dd, J=4.7 and 11.7 Hz, 1H), 7.4∼7.9(bs, 2H)

REFERENCE EXAMPLE 12

1a-Acetyl-7-demethoxy-6-demethyl-6,6-dichloro-6,7-dihydro-7-ethylenedioxymitomycin A (Compound "m")

53.4 mg of Compound "a" obtained in Reference Example 1 was dissolved in 5 ml of anhydrous tetrahydrofuran, and 30 μl of morpholine and 30 mg of N-chlorosuccinimide were added to the solution. The reaction mixture was stirred for 3 hours and 35 minutes at 25° C. and stirred for 2 hours and 15 minutes at 50° C. Then, 30 μl of morpholine and 30 mg of N-chlorosuccinimide were added to the solution, and the mixture was stirred for 4 hours and 15 minutes at 50° C.

The resultant reaction mixture was washed successively with a saturated sodium bicarbonate solution, phosphate buffer (pH4), and a saturated saline solution. The resultant solution was dried over anhydrous sodium sulfate. After the desiccant was removed by filtration, the solvent was distilled off. The residue obtained was purified by preparative TLC(silica gel; chloroform:methanol=6:1) to give a yellow zone. The zone was extracted and concentrated in a similar manner to that described in Example 7 to give 9.7 mg (yield 16%) of Compound "m" as a yellow powder.

TLC: Rf=0.53 (chloroform:acetonitrile:n-hexane=5:5:1)

FAB-MS(m/z): 476, 478, 480(M+ +1); $C_{18}H_{19}{}^{35}Cl_2N_3O_8$: 475

IR (cm$^{-1}$): 3470, 3360, 3200, 3070, 2940, 2900, 1730, 1710, 1690, 1670, 1570, 1340, 1270, 1190, 1070, 950

$^1$H-NMR: δ, ppm(270 MHz, pyridine-d$_5$) 2.10(s, 3H), 3.19(s, 3H), 3.4∼3.6(m, 2H), 3.8∼4.5(m, 7H), 4.71(bt, J=10.4 Hz, 1H), 5.72(dd, J=4.8 and 10.4 Hz, 1H), 7.4∼7.8(bs, 2H)

REFERENCE EXAMPLE 13

7-Demethoxy-6-demethyl-6,6-dibromo-6,7-dihydro-7-ethylenedioxymitomycin B (Compound "n")

1.00 g of Compound "c" obtained in Reference Example 3 was dissolved in 50 ml of anhydrous tetrahydrofuran, and 0.50 ml of diethylamine and 800 mg of N-bromosuccinimide were added to the solution. The reaction mixture was stirred for 25 minutes at ambient temperature.

The resultant reaction mixture was washed with phosphate buffer (pH7), and a saturated saline solution successively. The resultant solution was dried over anhydrous sodium sulfate. After the desiccant was removed by filtration, the solvent was distilled off under reduced pressure.

The residue obtained was purified by column chromatography (silica gel; chloroform:methanol=30:1) to obtain yellow fractions.

Fractions thus obtained were treated in a similar manner to that described in Example 5 to give 561 mg (yield 40%) of Compound "n" as a yellow powder.

TLC: Rf=0.26 (chloroform:methanol=9:1)

FAB-MAS(m/z): 522, 524, 526(M+ +1); $C_{16}H_{17}{}^{79}Br_2N_3O_7$: 521

IR (cm$^{-1}$): 3460, 3340, 3200, 2960, 2900, 1710, 1660, 1580, 1450, 1420, 1340, 1210, 1110, 1070, 1050

$^1$H-NMR: δ, ppm(270 MHz, pyridine-d$_5$) 2.19(s, 3H), 2.15∼2.25(m, 1H), 2.46(d, J=4.6 Hz, 1H), 3.39(dd, J=1.4 and 12.6 Hz, 1H), 3.55(d, J=12.5 Hz, 1H), 3.8∼4.0 (m, 2H), 4.1∼4.2(m, 1H), 4.41(dd, J=3.4 and 10.0 Hz, 1H), 4.45∼4.55(m, 1H), 5.22(bt, J=10.2 Hz, 1H), 5.42(dd, J=3.6 and 10.5 Hz, 1H), 7.2~7.6(br, 2H), 8.1~8.4(br, 1H)

What is claimed is:

1. A mitomycin derivative represented by the formula (I):

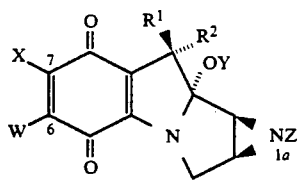

where
W represents halogen;
X represents methoxy, amino or ethylenimino;
Y represents hydrogen or methyl;
Z represents hydrogen or methyl; and
one of $R^1$ and $R^2$ represents carbamoyloxymethyl, the other represents hydrogen.

2. The mitomycin derivative according to claim 1, wherein
$R^1$ is carbamoyloxymethyl; and
$R^2$ is hydrogen; and
Y is methyl.

3. The mitomycin derivative according to claim 2, wherein Z is hydrogen.

4. The mitomycin derivative according to claim 3, wherein X is amino.

5. The mitomycin derivative according to claim 4, wherein W is chlorine.

6. The mitomycin derivative according to claim 4, wherein W is bromine.

* * * * *